United States Patent [19]
Ferrante

[11] Patent Number: 5,520,692
[45] Date of Patent: May 28, 1996

[54] ADJUSTABLE DEPTH PATELLA RECESSING GUIDE AND METHOD

[75] Inventor: Joseph M. Ferrante, Bartlett, Tenn.

[73] Assignee: Wright Medical Technology, Inc., Arlington, Tenn.

[21] Appl. No.: 395,479

[22] Filed: Feb. 28, 1995

[51] Int. Cl.⁶ .................................................. A61B 17/56
[52] U.S. Cl. ........................... 606/80; 606/79; 606/88; 606/96
[58] Field of Search ............................ 606/88, 87, 86, 606/89, 82, 80, 79, 96, 97, 102, 205, 206, 207, 167, 170, 172, 180; 128/754; 408/1 R, 3, 14, 85, 103, 104, 107, 115 R, 115 B, 72 B, 116, 241 G

[56] References Cited

U.S. PATENT DOCUMENTS

| | | | |
|---|---|---|---|
| 4,766,907 | 8/1988 | de Groot et al. | 128/754 |
| 5,019,104 | 5/1991 | Whiteside et al. | 623/20 |
| 5,129,907 | 7/1992 | Heldreth et al. | 606/80 |
| 5,147,365 | 9/1992 | Whitlock et al. | 606/88 |
| 5,342,364 | 8/1994 | Mikhail | 606/79 |
| 5,409,493 | 4/1995 | Greenberg | 606/96 |

OTHER PUBLICATIONS

Wright Medical Technology, Inc., 5677 Airline Rd., Arlington, TN 38002, (1993), *Total Condylar & Posterior Stabilized Surgical Technique*, 4 pages (front pages & pp. 26, 27 and 46). Author unknown.

*Primary Examiner*—Guy Tucker
*Attorney, Agent, or Firm*—Walker, McKenzie & Walker

[57] ABSTRACT

An adjustable depth patella recessing guide and method for guiding a cutting tool to recess the posterior surface of a patella. The guide includes a body having a first end for engaging the posterior surface of the patella, having a second end, and having a bore extending between the first and second ends for allowing the cutting tool to pass therethrough. A depth gauge is mounted within the bore of the body for movement in a direction between the first and second ends of the body. The depth gauge includes a stop for stopping the cutting tool. A lock mechanism is provided for locking the depth gauge to the body. The method includes the steps of clamping the body of the adjustable depth patella recessing guide to the posterior surface of the patella; placing the distal end of the cutting tool against the posterior surface of the body; then ascertaining the position of the cutting tool relative to the body; then locking the depth gauge to the body so that the depth gauge will stop the cutting tool a certain distance past the ascertained position of the cutting tool relative to the body; and then inserting the cutting tool into the posterior surface of the patella until stopped by the depth gauge.

12 Claims, 2 Drawing Sheets

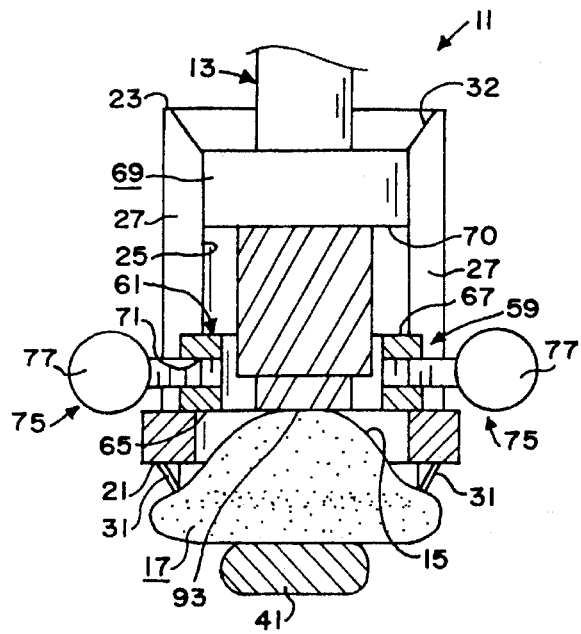
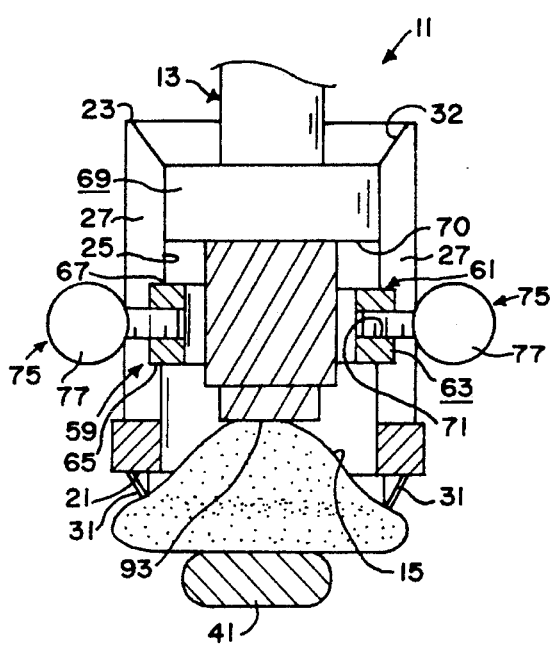
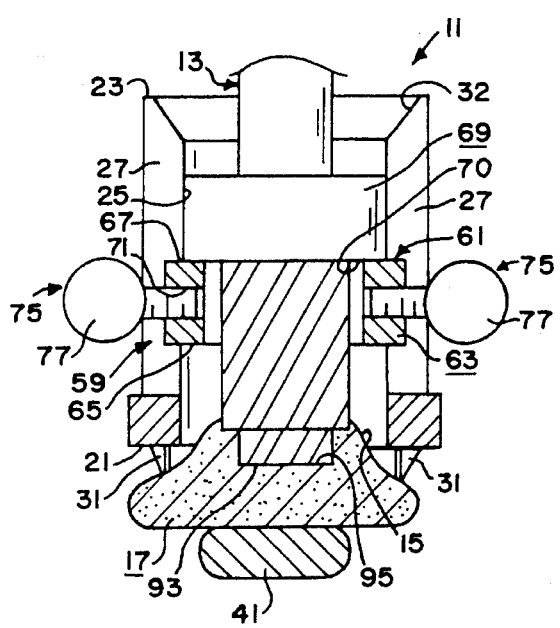
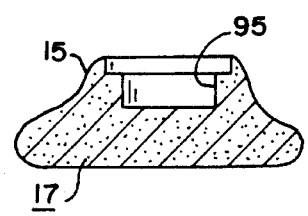
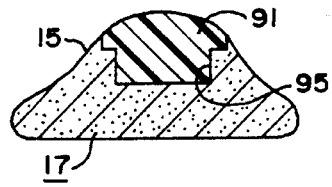

5,520,692

ADJUSTABLE DEPTH PATELLA RECESSING GUIDE AND METHOD

BACKGROUND OF THE INVENTION

1. Field of the Invention

The present invention relates, in general, to a guide for and a method of preparing a patella to receive a patellar prosthesis.

2. Background Art

The posterior surface of a healthy patella or knee-cap has two articular facets, lateral and medial, separated by a vertical ridge. The articular facets glide on the lateral and medial condyles of the femur while the vertical ridge fits into the groove between the condyles. Disease or trauma may degenerate or damage the posterior surface of a patella, causing pain and/or immobility of the knee joint. Various patellar implants and prostheses have been developed to replace the articulating surface of such patellas. See, for example, Whiteside et al., U.S. Pat. No. 5,019,104, issued May 28, 1991.

A patellar implant may be recessed into the posterior surface of a patella to help reproduce the patient's original patellar dome location and height while maintaining as much bone stock as possible. Such patellar implants are provided in different thicknesses and diameters. For example, patellar implants may be provided in various thicknesses ranging between 7 and 10 millimeters and in various diameters ranging between 25 and 32 millimeters to allow optimal patella repair.

An end mill, reamer or other cutting tool is typically used to recess or resect the posterior surface of the patella. If possible, the full thickness of the selected patellar implant should be removed from the patellar surface. Guides consisting of metal rings may be clamped onto the posterior surface of the patella to act as a stop to allow an end mill or the like to be inserted only a specific depth into the posterior surface of the patella, depending on the thickness of the ring.

Nothing in the known prior art discloses or suggests the present invention. For example, nothing in the known prior art discloses or suggests an adjustable depth patella recessing guide including a body having a first end for engaging the posterior surface of the patella, having a second end, and having a bore extending between the first and second ends for allowing the cutting tool to pass therethrough; a depth gauge mounted within the bore of the body for movement in a direction between the first and second ends of the body, the depth gauge including stop means for stopping the cutting tool; and lock means for locking the depth gauge to the body. Likewise, nothing in the known prior art discloses or suggests a method of recessing the posterior surface of a patella by clamping the body of the adjustable depth patella recessing guide to the posterior surface of the patella; placing the distal end of the cutting tool against the posterior surface of the body; then ascertaining the position of the cutting tool relative to the body; then locking the depth gauge to the body so that the depth gauge will stop the cutting tool a certain distance past the ascertained position of the cutting tool relative to the body; and then inserting the cutting tool into the posterior surface of the patella until stopped by the depth gauge.

SUMMARY OF THE INVENTION

The present invention provides a guide for and a method of recessing the posterior surface of a patella. A basic concept of the present invention is to provide such a guide and method that provides a positive stop for a cutting tool and that allows infinite depth adjustment of that positive stop.

The adjustable depth patella recessing guide of the present invention includes a body having a first end for engaging the posterior surface of the patella, having a second end, and having a bore extending between the first and second ends for allowing the cutting tool to pass therethrough; a depth gauge mounted within the bore of the body for movement in a direction between the first and second ends of the body, the depth gauge including stop means for stopping the cutting tool; and lock means for locking the depth gauge to the body.

The method of recessing the posterior surface of a patella of the present invention includes the steps of clamping the body of the adjustable depth patella recessing guide to the posterior surface of the patella; placing the distal end of the cutting tool against the posterior surface of the body; then ascertaining the position of the cutting tool relative to the body; then locking the depth gauge to the body so that the depth gauge will stop the cutting tool a certain distance past the ascertained position of the cutting tool relative to the body; and then inserting the cutting tool into the posterior surface of the patella until stopped by the depth gauge.

One object of the present invention is to provide a guide for use in, and a method of, preparing a patella to receive a patellar prosthesis which allows the posterior surface of a patella to be recessed to a preselected depth to restore the patella to its original thickness after a patellar implant is attached thereto.

Another object of the present invention is to provide such a guide having an adjustable stop to allow infinite depth adjustment and minimize error in replacement thickness.

Another object of the present invention is to provide such a guide that is calibrated on the outside to allow for accurate measurement for recessing depth.

BRIEF DESCRIPTION OF THE DRAWINGS

FIG. 4 is a sectional view substantially as taken on line 4—4 of FIG. 3 with a cutting tool shown combined therewith.

FIG. 5 is a sectional view similar to FIG. 4 but with the depth gauge shown in a moved position.

FIG. 6 is a sectional view similar to FIG. 5 but showing the cutting tool in a fully inserted position.

FIG. 7 is a sectional view of a patella, showing a recess cut into the posterior surface thereof.

FIG. 8 is a sectional view similar to FIG. 7 but showing a patellar implant applied to the patella.

DESCRIPTION OF THE PREFERRED EMBODIMENTS

Figure 1:
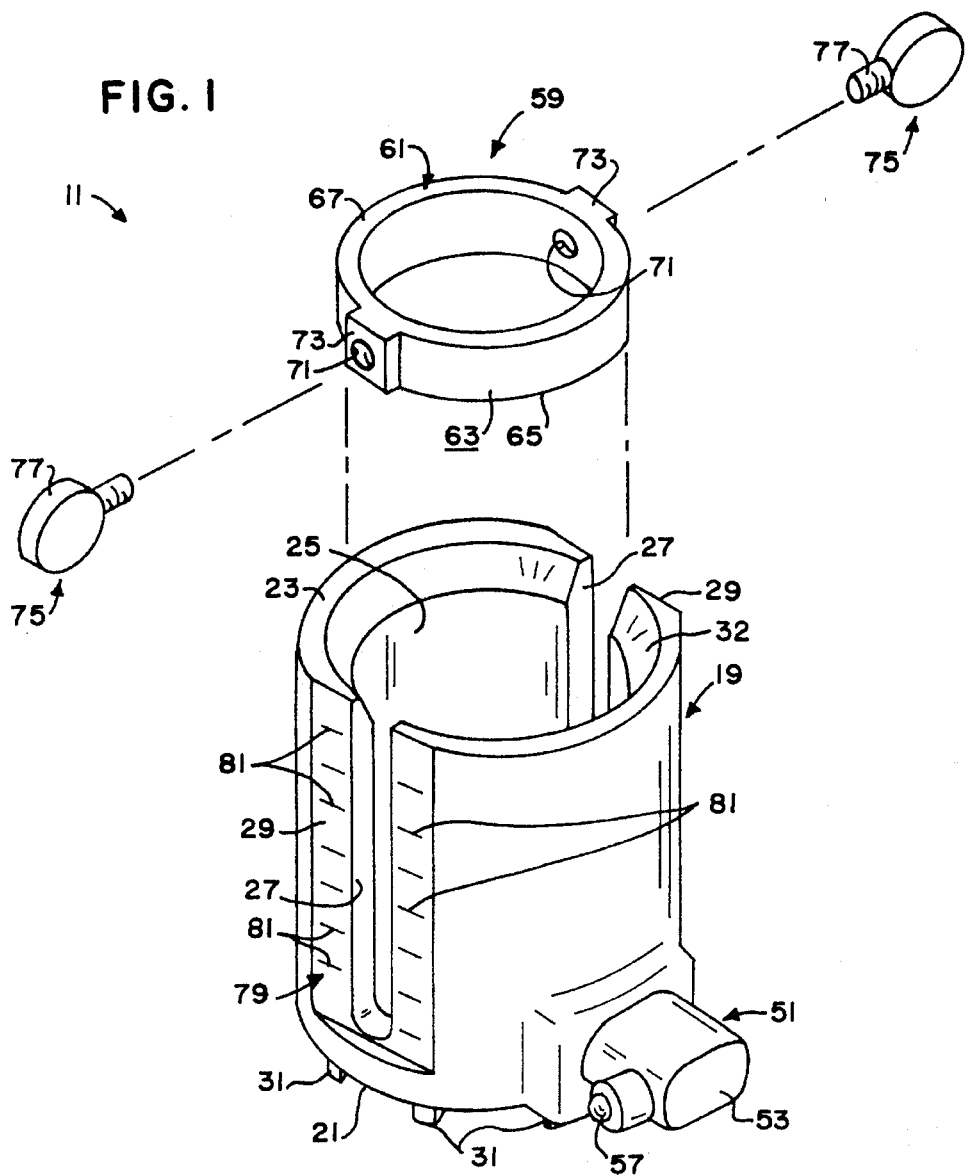
FIG. 1 is an exploded perspective view of the adjustable depth patella recessing guide of the present invention.

A first preferred embodiment of the adjustable depth patella recessing guide of the present invention is shown in FIGS. 1 and 3–6, and identified by the numeral 11. The adjustable depth patella recessing guide 11 is especially designed for guiding a cutting tool 13, such as an end mill or reamer, to recess the posterior surface 15 of a patella 17.

The adjustable depth patella recessing guide 11 includes a body 19 having a first end 21 for engaging the posterior surface 15 of the patella 17, having a second end 23, and having a bore 25 extending between the first and second ends 21, 23 for allowing the cutting tool 13 to pass therethrough. The body 19 preferably has a window therein opening into the bore 25. More specifically, the body 19 preferably includes two opposing slots 27 extending from the second end 23 thereof toward the first end 21 and passing from the exterior surface into the bore 25 for reasons which will hereinafter become apparent. Flats 29 may be machined on either side of the body 19 conterminous with each slot 27. A plurality of teeth 31 preferably extend from the first end 21 of the body 19 for securely gripping the posterior surface 15 of the patella 17. The end of the bore 25 adjacent the second end 23 of the body 19 may have a larger, flared portion 32.

The body 19 is preferably adapted to be clamped to the posterior surface 15 of the patella 17 via a clamp mechanism 33. The clamp mechanism 33 may be of various specific types and designs now apparent to those skilled in the art. Thus, for example, the clamp mechanism 33 may consist of a pliers-like structure including two elongated limbs joined together by a pivot with one end of each limb forming a pair of jaws and with the other end of each limb forming a pair of handles so that when the handles are moved toward one another, the jaws will likewise pivot toward one another. The body 19 could be attached to the one of such jaws. However, the clamp mechanism 33 preferably consists of a parallel-movement type clamp as shown generally in FIG. 3, including a first part 35 having a first jaw 37, including a second part 39 having a second jaw 41, and including drive or adjustment means 43 for moving the first and second parts 35, 39 toward one another to force the first and second jaws 37, 41 toward one another. The basic construction and operation of the clamp mechanism 33 may vary. Preferably, the first and second parts 35, 39 may be constrained to parallel movement by cross linkage means 45. The drive means 43 may consist simply of a threaded rod 47 having one end attached to the second part 39 and extending through an opening in the first part 35 with a nut 49 rotatably attached to the rod 47 above the opening in the first part 35 so that rotation of the nut 49 will effect movement of the first jaw 37 toward or away from the second jaw 41 as will now be apparent to those skilled in the art. On the other hand, the drive means 43 could consist of a ratchet mechanism or the like.

Attachment means 51 is preferably provided for securing the body 19 to the first jaw 37 so that movement of the first jaw 37 toward or away from the second jaw 41 will also cause the body 19 to move toward or away from the second jaw 41. The basic construction and operation of the attachment means 51 may vary. For example, that attachment means 51 may simply consist of a boss member 53 for extending into a cavity 55 in the first jaw 37, and a ball-type quick connect/disconnect means 57 for securing the boss member 53 within the cavity 55, etc., as will now be apparent to those skilled in the art.

The adjustable depth patella recessing guide 11 includes a depth gauge 59 mounted within the bore 25 of the body 19 for movement in a direction between the first and second ends 21, 23 of the body 19. The depth gauge 59 includes stop means 61 for stopping the cutting tool 13. More specifically, the depth gauge 59 may consist of a ring member 63 designed to slide up and down within the bore 25. The ring member 63 has a first end 65 directed toward the first end 21 of the body 19 and a second end 67 directed toward the second end 23 of the body 19. The stop means 61 is defined by the second end 67 of the ring member 63. More specifically, the second end 67 of the ring member 63 is sized to engage a flange or collar 69 of the cutting tool 13 when the cutting tool 13 is moved through the bore 25, thereby controlling the depth of insertion of the cutting tool 13 as will now be apparent to those skilled in the art. The collar 69 has a distal or reference edge 70. Threaded apertures 71 are preferably provided through opposite sides of the ring member 63. Protrusions 73 may be provided on opposites sides of the ring member 63 about each threaded aperture 71 for extending into the slots 27 in the body 19 and for assisting in aligning each threaded aperture 71 with one of the slots 27, etc.

The adjustable depth patella recessing guide 11 includes lock means 75 for locking the depth gauge 59 to the body 19. The lock means 75 may include a threaded bolt 77 for extending through one of the slots 27 in the body 19 and into one of the threaded apertures 71 in the ring member 63. The lock means 75 preferably includes a pair of such threaded bolts 77 for locking both sides of the ring member 63 to the body 19. Each bolt 77 may be a thumb screw or the like (i.e., may have an enlarged or flattened head) for allowing a surgeon to easily tighten or loosen the lock means 75 as will now be apparent to those skilled in the art.

The adjustable depth patella recessing guide 11 preferably includes gauge means 79 for allowing the position of the stop means 61 to be ascertained. The gauge means 79 may include a graduated scale 81 adjacent one or both slots 27 for allowing the position of the stop means 61 to be measured on the graduated scale 81. The graduated scale 81 may consist of a plurality of spaced reference marks formed in or on the flats 29 of the body 19 adjacent the sides of one or both slots 27. The gauge means 79 thus provides an indication or relative measurement of the location of the stop means 61 and/or the cutting tool 13. That is, a surgeon can merely visually align the end 67 of the ring member 63 (i.e., the stop means 61) or the reference edge 70 of the collar 69 through one of the slots 27 with one of the reference marks of the graduated scale 81 to determine the relative position thereof as will now be apparent to those skilled in the art. A corresponding reference mark (not shown) could be provided on each bolt 77 or on a washer or the like (not shown) positioned between the head of each bolt 77 and the body 19, etc., to assisting in making such relative measurement.

Figure 2:
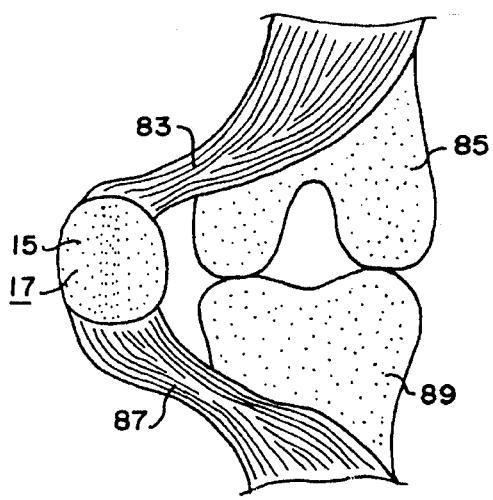
FIG. 2 is a somewhat diagrammatic front elevational view of a knee joint with the patella rotated to expose its posterior surface.
Figure 3:
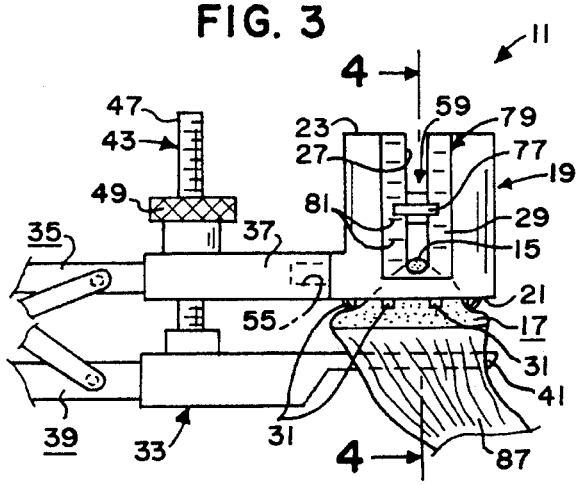
FIG. 3 is side elevational view of the adjustable depth patella recessing guide of the present invention shown mounted on one jaw of a parallel clamping mechanism and with a patella clamped thereto.

The method of recessing or resecting the posterior surface 15 of a patella 17 of the present invention starts with exposing the posterior surface 15 of the patella 17. This can be done in any typical manner well know to those skilled in the art. For example, a long anterior skin incision and medial parapatellar incision will allow the patella to be everted far laterally. In order to achieve good lateral position of the patella, it may be necessary to completely detach the oblique portion of the vastus medialis from the distal one-third of the quadriceps tendon. The patella 17 is shown in FIG. 2 twisted out of position to expose the posterior surface 15 thereof, with connective tissue 83 extending generally between the patella 17 and the femur 85, and with connective tissue 87 extending generally between the patella 17 and the tibia 89. The size of the patella 17 can be determined by measuring the thickness thereof with a calliper and measuring the diameter thereof with patellar templates or the like. The patellar template should cover the medial portion of the patella 15 as completely as possible, while allowing for a medial and superior wall to remain after reaming, etc. Once selected and positioned, the center of the template should be marked on the posterior surface 15 of the patella 17. A patellar implant 91 is selected. Peripheral osteophytes may be removed and the first end 21 of the body 19 clamped evenly to the posterior surface 15 of the patella 17, using the clamp mechanism 33 or the like, substantially centered with respect to any markings made on the posterior surface 15 relative to the center of the template, etc., or aligned over the patella 17 so that the patellar implant 91 will be medially positioned to lateralize the position of the patellar bone structure, helping to restore the natural Q-angle and stabilize patellar tracking as will be apparent to those skilled in the art. The bolts 77 are loosened so that the ring member 63 can be positioned adjacent the first end 21 of the body 19 (i.e., at the closed ends of the slots 27). The proper cutting tool 13 is selected, corresponding to the patellar diameter selected during templating, etc., and is inserted into the bore 25 until the distal end 93 thereof contacts the posterior surface 15 of the patella 17 as clearly shown in FIG. 4. The location of the reference edge 70 of the collar 69 is ascertained or read with respect to the graduated scale 81 by, for example, merely viewing the reference edge 70 through one of the slots 27 and comparing its position to the reference marks of the graduated scale 81. The depth gauge 59 is then set to proper position based on the noted location of the reference edge 70 of the collar 69 and the specific patellar implant 91 selected by merely sliding the ring member 63 within the bore 25 until the second end 67 thereof is aligned or adjacent the appropriate reference mark of the graduated scale 81 (see FIG. 5), and then tightening the bolts 77. Thus, for example, the second end 67 of the ring member 63 (i.e., the stop means 61) should be set or locked 14 millimeters below the previously determined reamer depth (i.e., the noted location of the reference edge 70 of the collar 69) for a high dome patellar implant. Likewise, the second end 67 is positioned 12 millimeters below the previously determined reamer depth for a low dome patellar implant, and 10 millimeters below the previously determined reamer depth for a metal-backed patellar implant. The cutting tool 13 is then allowed to come to full speed and then advanced into the bore 25 until the reference edge 70 of the collar 69 is opposed by the second end 67 of the ring member 63 as shown in FIG. 6, thereby cutting an appropriate recess 95 in the posterior surface 15 of the patella 17 as will now be apparent to those skilled in the art (see, in general, FIG. 7). The cutting tool 13 can then be removed from the body 19. Reaming is then complete for patellar implants that do not have pegs or the like for being inserted into the resected surface of the patella 17 (e.g., for most an all-polyethylene patellar implants). However, for patellar implants having pegs for being inserted into the resected surface of the patella 17 (e.g., certain metal-backed patellar implants), a drill guide (not shown) may be placed within the bore 25, flush with the resected surface of the patella 17 and various, relative small diameter (e.g., ⅛ inch) closed or blind end bores drilled into the resected surface of the patella 17 to receive the pegs, etc. The adjustable depth patella recessing guide 11 can then be removed from the patella 17 and any bone fragments removed. A trial patella implant can be applied and any osteophytes or overhanging surfaces removed with a rongeur or the like. The patellar retinaculum can then be closed with three towel clamps and patellar tracking checked as will be apparent to those skilled in the art. Once patellar tracking has been optimized in the normal manner, the trail patella implant is removed and the final patellar implant 91 inserted and anchored into place as shown in FIG. 8, using cement or the like. A final check should be made for osteophytes. A drain can be inserted and the knee can then be closed in the usual manner.

Although the present invention has been described and illustrated with respect to a preferred embodiment and a preferred use therefor, it is not to be so limited since modifications and changes can be made therein which are within the full intended scope of the invention.

I claim:

1. In combination, a cutting tool for recessing a posterior surface of a patella, said cutting tool having a distal end; and an adjustable depth patella recessing guide for guiding said cutting tool to recess said posterior surface of said patella; said guide comprising:

(a) a body having a first end for engaging said posterior surface of said patella, having a second end, and having a bore extending therethrough between said first and second ends thereof; said bore having a first mouth conterminous with said first end of said body and sized to allow at least a portion of said posterior surface of said patella to extend thereinto when said first end of said body engages said posterior surface of said patella; said bore having a second mouth conterminous with said second end of said body and sized to allow said distal end of said cutting tool to extend thereinto; said distal end of said cutting tool extending into said second mouth of said bore for engaging the portion of said posterior surface of said patella extending into said first mouth of said bore and for allowing the position of said cutting tool relative to said body when said distal end of said cutting tool engages said posterior surface of said patella to be noted;

(b) a depth gauge mounted within said bore of said body for movement in a direction between said first and second ends of said body, said depth gauge including stop means for stopping said cutting tool; and (c) lock means for locking said depth gauge to said body in a position so that said depth gauge will stop said cutting tool a predetermined distance past the noted position of said cutting tool relative to said body when said distal end of said cutting tool engages said posterior surface of said patella.

2. The adjustable depth patella recessing guide of claim 1 in which said lock means includes a bolt for locking said depth gauge to said body.

3. The adjustable depth patella recessing guide of claim 1 in which said lock means includes a pair of bolts for locking said depth gauge to said body.

4. The adjustable depth patella recessing guide of claim 1 in which is included gauge means for allowing the position of said stop means to be ascertained.

5. The adjustable depth patella recessing guide of claim 4 in which said body has a window therein which allows the position of said stop means to be noted; and in which said gauge means includes a graduated scale adjacent said window for allowing the position of said stop means to be measured on said graduated scale.

6. The combination of claim 1 in which is included a clamp mechanism for clamping said body of said guide to said posterior surface of said patella.

7. The combination of claim 1 in which said guide includes means for preventing said first end of said depth gauge thereof from extending past said first end of said body thereof.

8. The combination of claim 1 in which said body of said guide includes two opposing slots extending from said second end thereof partway to said first end thereof; and in which said depth gauge of said guide includes two opposing protrusions for extending into said slots in said body.

9. The combination of claim 8 in which each of said slots has a closed end adjacent said first end of said body for coacting with said protrusions to prevent said first end of said depth gauge from extending past said first end of said body.

10. The combination of claim 1 in which said cutting tool has a reference edge; and in which said body of said guide has a window for allowing the relative position of said reference edge of said cutting tool to be noted when said distal end of said cutting tool engages said posterior surface of said patella within said bore.

11. A method of recessing the posterior surface of a patella; said method comprising the steps of:

(a) exposing the posterior surface of said patella;

(b) providing a cutting tool with a distal end;

(c) providing an adjustable depth patella recessing guide including a body; a depth gauge movably mounted on said body; and lock means for locking said depth gauge to said body;

(d) clamping said body of said adjustable depth patella recessing guide to said posterior surface of said patella;

(e) placing said distal end of said cutting tool against said posterior surface of said patella;

(f) then ascertaining the position of the cutting tool relative to said body;

(g) then locking said depth gauge to said body so that said depth gauge will stop said cutting tool a certain distance past the ascertained position of said cutting tool relative to said body; and (h) then inserting said cutting tool into said posterior surface of said patella until stopped by said depth gauge.

12. A method of recessing the posterior surface of a patella; said method comprising the steps of:

(a) exposing the posterior surface of said patella;

(b) providing a cutting tool with a distal end;

(c) providing an adjustable depth patella recessing guide including a body having a first end for engaging said posterior surface of said patella, having a second end, and having a bore extending between said first and second ends for allowing said cutting tool to pass therethrough; a depth gauge mounted within said bore of said body for movement between said first and second ends of said body, said depth gauge including stop means for stopping said cutting tool; and lock means for locking said depth gauge to said body;

(d) clamping said adjustable depth patella recessing guide to said patella with said first end of said body engaging said posterior surface of said patella;

(e) inserting said cutting tool into said bore of said body until said distal end of said cutting tool contacts the posterior surface of said patella;

(f) then ascertaining the position of said cutting tool in said bore of said body;

(g) then locking said depth gauge to said body so that said stop means will stop said cutting tool a certain distance past the ascertained position of said cutting tool in said bore of said body; and (h) then inserting said cutting tool into said bore of said body and into said posterior surface of said patella until said cutting tool is stopped by said stop means.

* * * * *